United States Patent
Fujiwara et al.

(10) Patent No.: US 9,446,055 B2
(45) Date of Patent: Sep. 20, 2016

(54) DISINTEGRATING PARTICLE COMPOSITION AND ORALLY RAPIDLY DISINTEGRATING TABLET

(75) Inventors: Keiichi Fujiwara, Ibaraki (JP); Tadashi Fukami, Kamiichi-machi (JP); Haruka Koizumi, Kamichi-machi (JP)

(73) Assignee: FUJI CHEMICAL INDUSTRY CO., LTD., Toyama (JP)

( * ) Notice: Subject to any disclaimer, the term of this patent is extended or adjusted under 35 U.S.C. 154(b) by 0 days.

(21) Appl. No.: 13/389,880

(22) PCT Filed: Aug. 11, 2010

(86) PCT No.: PCT/JP2010/063601
§ 371 (c)(1),
(2), (4) Date: Feb. 10, 2012

(87) PCT Pub. No.: WO2011/019045
PCT Pub. Date: Feb. 17, 2011

(65) Prior Publication Data
US 2012/0156261 A1    Jun. 21, 2012

(30) Foreign Application Priority Data
Aug. 11, 2009    (JP) .................... 2009-186646

(51) Int. Cl.
| *A61K 47/26* | (2006.01) |
| *A61K 31/167* | (2006.01) |
| *A61K 9/14* | (2006.01) |
| *A61K 31/616* | (2006.01) |
| *A61K 9/00* | (2006.01) |
| *A61K 9/20* | (2006.01) |

(52) U.S. Cl.
CPC .......... *A61K 31/616* (2013.01); *A61K 9/0056* (2013.01); *A61K 9/2018* (2013.01)

(58) Field of Classification Search
None
See application file for complete search history.

(56) References Cited

U.S. PATENT DOCUMENTS

| 2005/0106240 A1 | 5/2005 | Tanaka et al. |
| 2007/0275058 A1 | 11/2007 | Tanaka et al. |

FOREIGN PATENT DOCUMENTS

| EP | 1 523 974 | 4/2005 |
| EP | 1 674 083 | 6/2006 |
| JP | 10-120554 | 5/1998 |
| JP | 11-310539 | 11/1999 |
| JP | 2000/86537 | 3/2000 |
| JP | 2005-139168 | 6/2005 |
| JP | 2008-285434 | * 11/2008 |
| WO | 2005/037254 | 4/2005 |
| WO | 2005/37319 | 4/2005 |
| WO | 2007/029376 | 3/2007 |
| WO | 2007/29379 | 3/2007 |

OTHER PUBLICATIONS

International Preliminary Report on Patentability and Written Opinion issued Mar. 13, 2012 in International Application No. PCT/JP2010/063601, of which the present application is the national stage.
International Search Report issued Oct. 5, 2010 in International (PCT) Application No. PCT/JP2010/063601, of which the present application is the national stage.
Supplementary European Search Report issued Dec. 12, 2012 in corresponding European Application No. 10808228.0.
English abstract of JP 2005-139168, Jun. 2, 2005.
English abstract of JP 2000-086537, Mar. 28, 2000.
English abstract of JP 10-120554, May 12, 1998.
English abstract of JP 11-310539. Nov. 9, 1999.
English abstract of JP 2008-285434, Nov. 27, 2008.
European Office Action dated Mar. 29, 2016 in corresponding European Patent Application No. 10 808 228.0.

* cited by examiner

*Primary Examiner* — Tigabu Kassa
(74) *Attorney, Agent, or Firm* — Wenderoth, Lind & Ponack, L.L.P.

(57) ABSTRACT

There has been a need for an orally rapidly disintegrating tablet which has a good texture and taste in the oral cavity, such a sufficient hardness as not giving any worry of being chipped or dusted during production or transportation and good disintegrating properties in the oral cavity and can sustain a sufficient hardness even under humid conditions after opening. Disclosed are a disintegrating particle composition which is prepared by dispersing, in the presence of water, mannitol, xylitol, an inorganic excipient, a disintegrating agent and carmellose and drying, and an orally rapidly disintegrating tablet which comprises said disintegrating particle composition, an active substance and a disintegrating agent. The disintegrating tablet has a good texture and taste, an appropriate hardness and good disintegrating properties and can sustain a sufficient hardness under humid conditions.

9 Claims, No Drawings

DISINTEGRATING PARTICLE COMPOSITION AND ORALLY RAPIDLY DISINTEGRATING TABLET

TECHNICAL FIELD

The present invention relates to a disintegrating particle composition formed by dispersing mannitol, xylitol, inorganic excipients, disintegrants and carmellose in the presence of water, followed by drying, as well as an orally rapidly disintegrating tablet with high humidity resistance comprising the composition, an active ingredient and additive disintegrants.

BACKGROUND ART

Orally rapidly disintegrating tablets have been developed as a form which is easy to be taken by patients, elderly people, children, etc. who have difficulty in swallowing drugs, or is easy to be taken without water. The orally rapidly disintegrating tablets should have such a sufficient hardness as not being chipped or dusted during production or transportation of tablets or opening, and in addition, it is required that a disintegration time in the oral cavity is within about 60 seconds and a texture and taste in the oral cavity has no problem. There are more problems to be solved in the orally rapidly disintegrating tablets compared to normal tablets.

Specifically, a disintegration time and hardness are contradictory factors, and in general, disintegration times tend to be extended as molding pressures are increased for the purpose of the increase of hardness, and hardness tends to be decreased as molding pressures are decreased for the purpose of the shortening of disintegration times. Additionally, suppressing hardness degradations due to absorption of moisture is required upon opening in a room. Hardness degradations due to absorption of moisture tend to occur in orally disintegrating tablets, since the orally disintegrating tablets absorb water to disintegrate just after they have contact with water.

A quickly dispersible particle containing inorganic antiacid obtained by homogeneously dispersing an inorganic antiacid, a sugar alcohol and a disintegrant in aqueous medium which is rapidly dispersed and suspended upon being added in water (Patent Document 1), an orally rapidly disintegrating tablet comprising a pharmaceutical composition obtained by dispersing sugar and an inorganic compound in water and spray-drying (Patent Document 2), and a composition for an orally rapidly disintegrating tablet characterized by dispersing a disintegrant and an inorganic substance in complex particles of sugar in the presence of water (Patent Documents 3, 4, 5) have been known.

These conventional art documents disclose that particles obtained by dispersing and dissolving sugar, an inorganic substance and a disintegrant in water and spray-drying are used in an orally rapidly disintegrating tablet, but said orally rapidly disintegrating tablet has not had sufficient hardness (40N or more) during production and transportation, sufficient disintegrating properties in the oral cavity within 60 seconds, and has degraded in hardness under humid conditions after opening, etc. The conventional art documents do not disclose any disintegrating particle composition comprising mannitol, xylitol, an inorganic excipient, a disintegrant and carmellose, a process for preparing the same, and any orally rapidly disintegrating tablet comprising said composition.

[Patent document 1] JP-A-10-120554
[Patent document 2] JP-A-2000-86537
[Patent document 3] WO 2005/37319 pamphlet
[Patent document 4] WO 2005/37254 pamphlet
[Patent document 5] WO 2007/29376 pamphlet

DISCLOSURE OF INVENTION

Problems to be Solved by the Invention

The present invention is directed to provide a disintegrating particle composition and an orally rapidly disintegrating tablet which have an improved texture and taste in the oral cavity, such a sufficient hardness as not giving any worry during production or transportation and good disintegrating properties in the oral cavity and can sustain a sufficient hardness even under humid conditions after opening, compared to orally rapidly disintegrating tablets in the conventional art.

Means of Solving the Problems

According to extensive studies to achieve the above purpose, the present inventors have found a disintegrating particle composition which is prepared by homogeneously dispersing mannitol, xylitol, inorganic excipient(s), disintegrant(s) and carmellose in the presence of water and drying. The present inventors have also found an orally rapidly disintegrating tablet which has excellent disintegrating properties, such a sufficient hardness as not giving any worry during production or transportation and a sufficient texture and taste in the oral cavity and can sustain a sufficient hardness even after opening, which is prepared by mixing and compressing to mold the disintegrating particle composition together with an active ingredient, disintegrant(s) (referred to as additive disintegrant(s) hereinafter) and additives which are formulated in medicine.

Specifically, the present invention is the following (1) to (13).

(1) A disintegrating particle composition, which is prepared by dispersing inorganic excipient(s), disintegrant(s) and carmellose in complex particles which are composed of mannitol and xylitol, wherein
(a) mannitol is in the amount of 70 to 90 parts by weight;
(b) xylitol is in the amount of 1 to 10 parts by weight;
(c) the inorganic excipient(s) are in the amount of 1 to 20 parts by weight;
(d) the disintegrant(s) are in the amount of 1 to 25 parts by weight;
(e) carmellose is in the amount of 1 to 20 parts by weight, and the total amount of the ingredients (a) to (e) is 100 parts by weight.

(2) A disintegrating particle composition, which is prepared by homogeneously dispersing inorganic excipient(s), disintegrant(s) and carmellose in complex particles which are composed of mannitol and xylitol, wherein
(a) mannitol is in the amount of 70 to 90 parts by weight;
(b) xylitol is in the amount of 1 to 10 parts by weight;
(c) the inorganic excipient(s) are in the amount of 1 to 20 parts by weight;
(d) the disintegrant(s) are in the amount of 1 to 25 parts by weight;
(e) carmellose is in the amount of 1 to 20 parts by weight, and the total amount of the ingredients (a) to (e) is 100 parts by weight.

(3) A disintegrating particle composition, wherein the total amount of the ingredients (a) to (e) is 100 parts by weight, which is prepared by homogeneously dispersing
(a) 70 to 90 parts by weight of mannitol;
(b) 1 to 10 parts by weight of xylitol;
(c) 1 to 20 parts by weight of inorganic excipient(s);
(d) 1 to 25 parts by weight of disintegrant(s); and (e) 1 to 20 parts by weight of carmellose in the presence of water, followed by drying.

(4) A disintegrating particle composition, wherein the total amount of the ingredients (a) to (e) is 100 parts by weight, which is obtainable by spray-drying a dispersion comprising
(a) 75 to 85 parts by weight of mannitol;
(b) 1 to 5 parts by weight of xylitol;
(c) 2 to 14 parts by weight of inorganic excipient(s);
(d) 2 to 20 parts by weight of disintegrant(s); and
(e) 2 to 15 parts by weight of carmellose.

(5) The disintegrating particle composition of (2), wherein
(a) mannitol is in the amount of 75 to 85 parts by weight;
(b) xylitol is in the amount of 1 to 5 parts by weight;
(c) inorganic excipient(s) are in the amount of 2 to 14 parts by weight;
(d) disintegrant(s) are in the amount of 2 to 20 parts by weight;
(e) carmellose is in the amount of 2 to 15 parts by weight, and the total amount of the ingredients (a) to (e) is 100 parts by weight.

(6) The disintegrating particle composition of any one of (1) to (5), wherein the inorganic excipient(s) are in the average particle size of 0.1 to 300 μm and are at least one or more agents selected from magnesium carbonate, calcium carbonate, calcium phosphate, calcium hydrogen phosphate, anhydrous calcium hydrogen phosphate, an agglomerated material of anhydrous calcium hydrogen phosphate, magnesium aluminometasilicate, magnesium aluminosilicate, hydrotalcite, aluminum silicate, calcium silicate, magnesium silicate, anhydrous silicic acid, silicon dioxide, magnesium oxide, magnesium hydroxide, magnesium hydroxide-aluminium hydroxide co-precipitate, dried aluminum hydroxide gel or talc.

(7) The disintegrating particle composition of any one of (1) to (5), wherein the disintegrant(s) are at least one or more agents selected from crospovidone, low-substituted hydroxypropylcellulose, croscarmellose sodium or crystalline cellulose.

(8) A process for preparing the disintegrating particle composition of any one of (1) to (7), comprising a step wherein the ingredients (a) to (e) are granulated in the presence of water.

(9) A process for preparing the disintegrating particle composition of any one of (1) to (7), comprising a step wherein a dispersion comprising the ingredients (a) to (e) is sprayed.

(10) A process for preparing the disintegrating particle composition of any one of (1) to (7), comprising a step wherein a dispersion comprising the ingredients (a) to (e) is spray-dried.

(11) An orally rapidly disintegrating tablet, comprising the disintegrating particle composition of any one of (1) to (7), wherein hardness after accelerated test under humidified condition is 25N or more.

(12) An orally rapidly disintegrating tablet, comprising 0.01 to 200 parts by weight of an active ingredient and 10 to 200 parts by weight of additive disintegrant(s) per 100 parts by weight of the disintegrating particle composition of any one of (1) to (7).

(13) The orally rapidly disintegrating tablet of (12), wherein the additive disintegrant(s) are at least one or more agents selected from hydroxypropyl starch, crystalline cellulose, carmellose sodium, crospovidone, cornstarch, waxy cornstarch, rice starch, sticky rice starch, potato starch, flour starch, sweet potato starch or tapioca starch.

Effect of Invention

The orally rapidly disintegrating tablet comprising the disintegrating particle composition of the present invention is characterized by suppressing hardness degradations under humid conditions after opening and having such a sufficient hardness as not giving any worry during production or transportation and good disintegration times in the oral cavity, compared to conventional orally rapidly disintegrating tablets comprising sugar, inorganic excipient(s) and disintegrant(s). Accordingly, an orally rapidly disintegrating tablet comprising the desired active ingredient may be used in medicine or food which rapid disintegrating properties in the oral cavity are required.

BEST MODE FOR CARRYING OUT THE INVENTION

The disintegrating particle composition of the present invention is a spherical particulate composition which is prepared by dispersing inorganic excipient(s), disintegrant(s) and carmellose in complex particles which are composed of mannitol and xylitol, preferably the composition wherein the dispersing is homogeneous dispersing. The "complex particles" composed of mannitol and xylitol refer to particles wherein xylitol is solid-dispersed in mannitol particles. The "dispersing in complex particles" is observed by SEM images (scanning electron micrograph), etc., preferably "homogeneously dispersing in complex particles". The "homogeneously dispersing in complex particles" refers to a state wherein each ingredient which is identifiable by SEM images, etc. is dispersed in smaller particle sizes close to primary particles than apparent particle sizes upon addition in complex particles. The apparent particle sizes refer to average particle sizes measured by a dry particle size distribution analyzer without pretreatment before dispersion.

Among sugar, mannitol is easy to use, since it is stable as an excipient in that it is not hygroscopic, it is not colored by a reaction such as Maillard reaction and it is poorly reactive with agents, but it is disadvantageous in that its molding properties are bad. The disintegrating particle composition of the present invention has good molding properties and disintegrating properties as well as temporal stabilities by solid-dissolving or solid-dispersing xylitol into part or all of mannitol to prepare a complex base. These factors are described in JP-A-2005-139168 in detail.

The complex particles composed of mannitol and xylitol include those which form a solid dispersion. It can be confirmed that the complex particles form a solid dispersion, since a melting point decreases by 0.5 to 19° C. The complex particles become a state that parts of mannitol molecules are replaced with xylitol molecules in the crystalline structure of mannitol, or a state that xylitol molecules get into vacancies of the crystalline structure of mannitol to produce distortion in the crystalline structure of mannitol, and become higher energy state in enthalpy than normal crystal of mannitol alone. Said higher energy state of mannitol in the disintegrating particle composition of the present invention can provide high molding properties, rapid disintegrating properties and tablet hardness suitable for a composition for an orally rapidly disintegrating tablet to mannitol which has normally less molding properties, rapid disintegrating properties and tablet strength as a composition for an orally rapidly disintegrating tablet.

The average particle size of the disintegrating particle composition of the present invention may be 1 to 400 μm, preferably 5 to 300 μm, in view of preventing roughness in the oral cavity and disintegrating properties. In view of the disintegrating properties in the oral cavity, fluidity during preparation of tablet and loading properties, the more spherical the disintegrating particle composition of the present invention is, the more preferable it is, and the degree of sphericity is 0.7 or more, more preferably 0.8 or more. The degree of sphericity is calculated by ratios of minor axis/major axis in SEM images or optical microscope. The average particle size of the disintegrating particle composition of the present invention obtained above is measured by Laser Diffraction Particle Size Analyzer [HELOS & RODOS] of SYMPATEC, Inc., for example.

The static specific volume of the composition of the present invention is preferably 1.5 to 4.0 ml/g, more preferably 1.5 to 3.5 ml/g, further preferably 1.5 to 2.5 ml/g. Such a static specific volume can achieve ease of mixing with other ingredients, smoothness during formulation due to ease of loading into mortar during molding tablet, and excellent tableting properties to provide homogeneous compression of tablet. The static specific volume may be measured in accordance with conventional methods.

The inorganic excipient in the present invention is particulate powders wherein the average particle size is 0.1 to 300 μm, which is insoluble or hardly soluble in water and has high-specific surface areas, and is, for example, at least one or more agents selected from magnesium carbonate, calcium carbonate, calcium phosphate, calcium hydrogen phosphate, anhydrous calcium hydrogen phosphate, an agglomerated material of anhydrous calcium hydrogen phosphate, magnesium aluminometasilicate, magnesium aluminosilicate, hydrotalcite, aluminum silicate, calcium silicate, magnesium silicate, anhydrous silicic acid, silicon dioxide, magnesium oxide, magnesium hydroxide, magnesium hydroxide-aluminium hydroxide co-precipitate, dried aluminum hydroxide gel or talc. Preferable one is at least one or more agents selected from magnesium aluminometasilicate, magnesium aluminosilicate, anhydrous silicic acid, calcium silicate, calcium phosphate, calcium hydrogen phosphate, anhydrous calcium hydrogen phosphate, calcium carbonate, hydrotalcite or talc.

It is preferable that the inorganic excipient has high-specific surface areas in view of water-conducting properties or dispersibilities in complex particles, and BET-specific surface area is 10 to 500 $m^2/g$ and a preferable BET-specific surface area is 20 to 500 $m^2/g$. It is considered that one having high-specific surface areas improves permeabilities of water in granulated particles by water-conducting effects and disrupts granulated particles immediately in contact with water due to its aggregated structure of a few micrometers or less of primary particles. When an inorganic excipient with high-specific surface areas is used to compress and mold into a tablet form in the production of the granulated particles of the present invention, the inorganic excipient reduces the water content of sugar by adjusting concentrations of water in a tablet. Binding forces at junction points of disintegrating particle compositions proceed to reduce under humid conditions after opening by the adjusting effect. When an inorganic excipient is used, the granulation efficiency by spray may be improved and the yields of the disintegrating particle composition of the present invention may be improved.

The disintegrant(s) in the present invention are one or more agents selected from crospovidone, low-substituted hydroxypropylcellulose, croscarmellose sodium, carmellose sodium, carmellose calcium, crystalline cellulose, powdered cellulose, hydroxypropyl starch or starch. Preferable one is one or more agents selected from crospovidone, low-substituted hydroxypropylcellulose, croscarmellose sodium or crystalline cellulose, more preferably low-substituted hydroxypropylcellulose.

Carmellose is also known as carboxymethyl cellulose, and is a cellulose derivative which is swelled by the addition of water to form a viscous suspension. Its use includes base, binder, suspending agent, adhesive, excipient, disintegrant. A combination use of carmellose with disintegrant can achieve an improved disintegrating activity. Carmellose may also suppress hardness loss caused under humid conditions in the orally rapidly disintegrating tablet of the present invention. Any commercially available carmellose including NS-300 manufactured by Nichirin Chemical Industries, Ltd., Cellogen P manufactured by Dai-ichi Kogyo Seiyaku Co., Ltd. may be used in the present invention.

Mannitol with 0.1 to 500 μm of the average particle size, preferably 0.1 to 200 μm of the average particle size, may be used for the purpose of preventing roughness in the oral cavity. Since an inorganic excipient, disintegrant and carmellose are insoluble in water, those with 0.1 to 60 μm of the average particle size, preferably 0.1 to 20 μm or less of the average particle size, may be used for the purpose of the dispersion in the composition of the present invention or the prevention of roughness in the oral cavity. Xylitol with any particle sizes may be used, since it is readily soluble.

The blending amounts of each ingredient in the composition of the present invention is 70 to 90 parts by weight of mannitol, 1 to 10 parts by weight of xylitol, 1 to 20 parts by weight of an inorganic excipient, 1 to 25 parts by weight of a disintegrant, and 1 to 20 parts by weight of carmellose, per 100 parts by weight of the total amount of the ingredients (a) to (e), preferably 75 to 85 parts by weight of mannitol, 1 to 5 parts by weight of xylitol, 2 to 14 parts by weight of an inorganic excipient, 2 to 20 parts by weight of a disintegrant, and 2 to 15 parts by weight of carmellose, per 100 parts by weight of the total amount of the ingredients (a) to (e), particularly preferably 76 to 80 parts by weight of mannitol, 1 to 3 parts by weight of xylitol, 3 to 9 parts by weight of an inorganic excipient, 5 to 18 parts by weight of a disintegrant, and 5 to 15 parts by weight of carmellose, per 100 parts by weight of the total amount of the ingredients (a) to (e).

The composition of the present invention may comprise the following active ingredient and other ingredients to be blended without impairing disintegrating properties, if needed, and the blending amount of each ingredient is 0.01 to 200 parts by weight of the active ingredient and 0.1 to 200 parts by weight of other ingredients to be blended without impairing disintegrating properties per 100 parts by weight as the sum of mannitol, xylitol, an inorganic excipient, a disintegrant and carmellose, preferably 0.1 to 100 parts by weight of the active ingredient and 0.1 to 100 parts by weight of other ingredients to be blended without impairing disintegrating properties per 100 parts by weight as the sum of mannitol, xylitol, an inorganic excipient, a disintegrant and carmellose.

The composition of the present invention may be usually prepared by any methods wherein a complex is formed by dispersing each insoluble ingredient in the presence of water to dry, specifically any wet-granulation methods including atomizing methods such as spray drying, tumbling granulation, agitation granulation, fluidized-bed granulation, freeze-drying methods, kneading granulation. Since mannitol, xylitol, an inorganic excipient, a disintegrant and carmellose of the element of the present invention are hydrophilic, these are dispersed from aggregated states of dry powders to monodispersed states of particles by physical operations such as stirring in the presence of water by wet granulation. Atomizing methods such as spray drying, tumbling granulation, agitation granulation or fluidized-bed granulation wherein dispersion can be readily carried out and drying can be carried out by spraying with rapid drying rate are preferable, and particularly, spray drying method which enables continuous production is most preferable.

The composition of the present invention may be prepared by dispersing mannitol, xylitol, an inorganic excipient, a disintegrant and carmellose into an aqueous solvent and spraying the dispersion to granulate according to the conventional method, or by spraying the dispersion to carriers such as mannitol according to the conventional method. A dosing order in preparing the dispersion is not specified, but it is preferable that mannitol and xylitol are preliminarily dissolved or dispersed in an aqueous solvent, followed by an inorganic excipient, a disintegrant and carmellose are homogeneously dispersed to prepare. The disintegrating particle composition of the present invention may be prepared by mixing an active ingredient with other ingredients to be blended without impairing disintegrating properties to give a dispersion and spraying the dispersion.

The above solvent may be any solvent which do not affect properties of the composition and may be acceptable for pharmaceuticals or foods, and includes water, ethanol, methanol, acetone, for example. The dispersion may be prepared according to the known method which includes conventional stirring, colloid milling, high-pressure homogenizing, ultrasonic irradiation, for example, and may be any methods which may highly disperse particles in an aqueous dispersion. The concentration of the composition in the dispersion may be any concentration which may maintain viscosity to be able to deliver or spray-drying the dispersion and may be any economic concentration, specifically 5 to 50% by weight, preferably 10 to 45% by weight.

Conditions of spray-drying are not limited, but a preferable spray-drying system is disk or nozzle type. The temperature in the spray-drying is preferably about 120 to 300° C. at inlet temperature, and about 80 to 130° C. at outlet temperature. The concentration of solid materials in the aqueous dispersion in the spray drying may be any concentrations which spray drying may be carried out. The particle size of the composition may be optionally controlled by concentrations of an aqueous solution or aqueous dispersion, spray-drying systems, drying conditions.

The "orally rapidly disintegrating tablet" in the present invention refers to a tablet which may rapidly disintegrate in the oral cavity, for example within 60 seconds, preferably within 40 seconds, most preferably within 30 seconds. The disintegration time in the oral cavity herein is time needed in the following conditions of the orally rapidly disintegrating tablet or Example methods. The disintegration time in the oral cavity differs between tablets depending on the size or figure of tablet, which is also included in the present invention.

In the present invention, the "texture" which does not generate discomfort in the oral cavity refers to the feeling without causing mealy texture or muddy smell which does not cause a feeling wherein blending materials just absorb water to swell and a tablet does not disintegrate, i.e. without fluffy feelings, and the "taste" which does not generate discomfort in the oral cavity refers to the feeling without tartness (i.e., sourness), bitter taste, hard taste derived from starting materials.

The orally rapidly disintegrating tablet of the present invention may comprise the composition of the present invention and an active ingredient, an additive disintegrant and other ingredients to be blended without impairing disintegrating properties. The blending ratio of each ingredient is 0.01 to 200 parts by weight of an active ingredient, 10 to 200 parts by weight of an additive disintegrant and 0.1 to 100 parts by weight of other ingredients to be blended without impairing disintegrating properties per 100 parts by weight of the total amount of the ingredients (a) to (e), preferably 0.1 to 100 parts by weight of an active ingredient, 25 to 55 parts by weight of an additive disintegrant and 1 to 50 parts by weight of other ingredients to be blended without impairing disintegrating properties per 100 parts by weight of the disintegrating particle composition. The blending ratios of the additive disintegrant to be blended and other ingredients to be blended without impairing disintegrating properties vary according to properties of the active ingredient, but the variability of the blending ratios is also included in the present invention.

In the present invention, the additive disintegrant is, for example, one or more agents selected from adipic acid, alginic acid, sodium alginate, pregelatinized starch, erythritol, fructose, sodium carboxymethyl starch, carmellose, carmellose calcium, carmellose sodium, aqueous silicon dioxide, agar, xylitol, guar gum, calcium citrate, croscarmellose sodium, crospovidone, synthetic aluminum silicate, magnesium aluminosilicate, low-substituted hydroxypropylcellulose, crystalline cellulose, crystalline cellulose carmellose sodium, cornstarch, waxy cornstarch, flour starch, sweet potato starch, tapioca starch, rice starch, sticky rice starch, cellulose acetate phthalate, dioctyl sodium sulfosuccinate, sucrose fatty acid ester, magnesium hydroxide-aluminium hydroxide co-precipitate, calcium stearate, polyoxyl stearate, sorbitan sesquioleate, gelatin, shellac, sorbitol, sorbitan fatty acid ester, talc, sodium hydrogen carbonate, magnesium carbonate, precipitated calcium carbonate, dextrin, sodium dehydroacetate, tragacanth, trehalose, lactose, maltose, saccharose, hydrotalcite, honey, palatinit, palatinose, potato starch, hydroxyethylmethylcellulose, hydroxypropyl starch, hydroxypropylcellulose, glucose, bentonite, partially pregelatinized starch, monosodium fumarate, polyethylene glycol, polyoxyethylene hardened castor oil, polyoxyethylene polyoxypropylene glycol, polysorbate, polyvinyl acetal diethylamino acetate, polyvinylpyrrolidone, maltitol, D-mannitol, anhydrous citric acid, anhydrous silicic acid, magnesium aluminometasilicate, methylcellulose, glycerin monostearate or sodium lauryl sulfate, and any one of them may be used alone and two or more of them may be mixed. Preferable one is crospovidone, hydroxypropyl starch, cornstarch, waxy cornstarch, rice starch, sticky rice starch, potato starch, flour starch, sweet potato starch or tapioca starch.

In the present invention, the active ingredient refers to an active principle for medicament or a nutrient component in food. The active ingredient may be added alone, or in the sustained releasable form or the coated or granulated form of the active ingredient so as to mask bitter taste. The coating processing includes a method spray drying the active ingredient and agents such as an insoluble polymer, stomach-soluble polymer, enteric polymer, a method mixing the active ingredient with methylcellulose and mannitol.

Specific coating methods of the active ingredient include, for example, a method of JP-A-11-263723 wherein the active ingredient is spray-dryed, fluidized-bed granulated, agitation-granulated, kneading-granulated with a readily soluble ingredient such as xylitol, sorbitol, sucrose, a water-soluble binder such as polyvinylpyrrolidone, pullulan, hydroxypropylcellulose, hydroxypropyl methylcellulose, gum arabic, gelatin, and an excipient such as mannitol, lactose, mannose to coat the active ingredient. A method of JP-A-2002-275054 wherein the active ingredient is coated with gelling agent, binder and sugar alcohol is also included.

The active ingredient is not limited, and includes central nervous system agents, peripheral nervous system agents, agents affecting sensory organs, agents affecting circulatory organs, agents affecting respiratory organs, agents affecting digestive organs, hormonal agents, agents affecting genito-urinary apparatus, medicaments affecting other organs, vitamin preparations, revitalizers, agents for blood or body fluid, other metabolized drugs, cellular stimulants, antineoplastic agents, radioactive agents, anti-allergic agents, other medicaments for tissue cellular functions, natural medicine, Chinese medicine, other natural medicine and medicine based on Chinese medicine prescription, antibiotic agents, chemotherapeutic agents, biological preparations, agents against parasitic animals, other medicine against pathogenic organism, dispensing agents, diagnostic agents, agents for public health, extracorporeal diagnostic agents, other agents not mainly intended for treatment, alkaloidal narcotics (i.e., natural narcotics), and non-alkaloidal narcotics (Drugs in Japan 2008, Jihou, Inc.).

Hypnosedatives or anti-anxiety agents among the central nervous system agents include alprazolam, estazoram, dexmedetomidine hydrochloride, rilmazafone hydrochloride, oxazolam, quazepam, tandospirone citrate, cloxazolam, clorazepate dipotassium, chlordiazepoxide, diazepam, potassium bromide, calcium bromide, sodium bromide, zolpidem tartrate, secobarbital sodium, zopiclone, tofisopam, triazolam, triclofos sodium, nitrazepam, nimetazepam, passiflora extract, barbital, haloxazolam, phenobarbital, prazepam, fludiazepam, flutazolam, flutoprazepam, flunitrazepam, flurazepam hydrochloride, brotizolam, bromazepam, bromovalerylurea, pentobarbital, chloral hydrate, midazolam, mexazolam, medazepam, ethyl loflazepate, lorazepam, lormetazepam.

Antiepileptic agents include acetylpheneturide, gabapentin, carbamazepine, clonazepam, clobazam, sultiame, zonisamide, trimethadione, sodium valproate, phenytoin, primidone.

Antipyretics, analgesics or antiphlogistics include actarit, aspirin, acetaminophen, ampiroxicam, ibuprofen, indomethacin, indomethacin farnesyl, ethenzamide, etodolac, epirizole, emorfazone, tramadol hydrochloride, buprenorphine hydrochloride, oxaprozin, ketoprofen, sodium salicylate, zaltoprofen, diclofenac sodium, sulindac, sulpyrine hydrate, celecoxib, tiaprofenic acid, tiaramide hydrochloride, tenoxicam, naproxen, bucolome, pentazocin, mefenamic acid, meloxicam, mofezolac, loxoprofen sodium hydrate.

Antiparkinson agents include amantadine hydrochloride, selegiline hydrochloride, talipexole hydrochloride, piroheptine hydrochloride, pramipexole hydrochloride hydrate, mazaticol hydrochloride, metixene hydrochloride, entacapone, cabergoline, trihexyphenidyl hydrochloride, droxidopa, biperiden, bromocriptine mesilate, pergolide mesilate, levodopa.

Psychoneurotic agents include amitriptyline hydrochloride, amoxan, aripiprazole, imipramine hydrochloride, etizolam, sultopride hydrochloride, sertraline hydrochloride, trazodone hydrochloride, paroxetine hydrochloride hydrate, floropipamide hydrochloride, perospirone hydrochloride hydrate, mianserin hydrochloride, milnacipran hydrochloride, methylphenidate hydrochloride, mosapramine hydrochloride, moperone hydrochloride, lofepramine hydrochroride, oxypertine, olanzapine, carpipramine, clocapramine hydrochloride hydrate, clotiazepam, clomipramine hydrochloride, chlorpromazine, spiperone, sulpiride, zotepine, lithium carbonate, timiperone, haloperidol decanoate, nemonapride, nortriptyline hydrochloride, haloperidol, hydroxyzine hydrochloride, hydroxyzine pamoate, pimozide, quetiapine fumarate, fluphenazine, prochlorperazine, propericiazine, bromperidol, perphenazine, maprotiline hydrochloride, setiptiline maleate, trifluoperazine maleate, trimipramine maleate, fluvoxamine maleate, modafinil, risperidone, levomepromazine.

Other central nervous system agents include tiapride hydrochloride, donepezil hydrochloride, taltirelin hydrate, terguride, mazindol, riluzole.

Regional anesthetics among the peripheral nervous system agents include ethyl aminobenzoate, bupivacaine hydrochloride, ropivacaine hydrochloride hydrate, oxethazaine, procaine hydrochloride, mepivacaine hydrochloride, lidocain.

Autonomic agents include ambenonium chloride, oxapium iodide, distigmine bromide, propantheline bromide, mepenzolate bromide.

Spasmolytic agents include afloqualone, eperisone hydrochloride, piperidolate hydrochloride, tizanidine hydrochloride, timepidium bromide hydrate, tolperisone hydrochloride, baclofen, papaverine hydrochloride, butylscopolamine bromide, butropium bromide, flopropione, N-methylscopolamine methylsulfate.

Otological agents among agents affecting sensory organs include amlexanox, lomefloxacin hydrochloride, ofloxacin, chloramphenicol. Antimotionsickness agents include isoproterenol hydrochloride, diphenidol hydrochloride, betahistine mesylate.

Cardiotonic agents among agents affecting circulatory organs include aminophylline hydrate, etilefrine hydrochloride, isoproterenol hydrochloride, choline theophylline, digitoxin, digoxin, denopamine, pimobendan, proxyphylline, vesnarinone, methyldigoxin, ubidecarenone.

Antiarrhythmic agents include ajimarine, acebutolol hydrochloride, atenolol, alprenolol hydrochloride, arotinolol hydrochloride, aprindine hydrochloride, amiodarone hydrochloride, sotalol hydrochloride, pilsicainide hydrochloride, propafenone hydrochloride, bepridil hydrochloride, oxprenolol hydrochloride, carteolol hydrochloride, quinidine sulfate hydrate, cibenzoline succinate, flecainide acetate, disopyramide, nadolol, pindolol, bufetolol hydrochloride, bisoprolol fumarate, procainamide hydrochloride, propranolol hydrochloride, verapamil hydrochloride, mexiletine hydrochloride.

Diuretics include azosemide, chlorthalidone, spironolactone, torasemide, triamterene, trichlormethiazide, hydrochlorothiazide, piretanide, bumetanide, furosemide, benzylhydrochlorothiazide, mefruside, mozavaptan hydrochloride.

Hypotensive agents include azelnidipine, alacepril, aranidipine, indapamide, amosulalol hydrochloride, imidapril hydrochloride, efonidipine hydrochloride, quinapril hydrochloride, celiprolol hydrochloride, tilisolol hydrochloride, temocapril hydrochloride, terazosin hydrochloride, delapril hydrochloride, barnidipine hydrochloride, prazosin hydrochloride, betaxolol hydrochloride, benazepril hydrochloride, bevantolol hydrochloride, manidipine hydrochloride, labetalol hydrochloride, olmesartan medoxomil, cadralazine, captopril, carteolol hydrochloride, carvedilol, candesartan cilexetil, guanabenz acetate, clonidine hydrochloride, cilazapril, cilnidipine, telmisartan, todralazine hydrochloride hydrate, trandolapril, tripamide, nicardipine hydrochloride, nipradilol, nilvadipine, valsartan, hydralazine hydrochloride, pindolol, felodipine, budralazine, bunazosin hydrochloride, propranolol hydrochloride, perindopril erbumine, penbutolol sulfate, enalapril maleate, bopindolol malonate, doxazosin mesilate, meticrane, methyl-DOPA hydrate, metoprolol tartrate, lisinopril hydrate, rescinnamine, reserpine, losartan potassium.

Vasoconstrictive agents include rizatriptan benzoate, midodrine hydrochloride, dihydroergotamine mesylate, eletriptan hydrobromide, sumatriptan, zolmitriptan.

Vasodilators include isosorbide mononitrate, inositol hexanicotinate, isoxsuprine hydrochloride, dipyridamole, isosorbide dinitrate, dilazep hydrochloride hydrate, diltiazem hydrochloride, trapidil, trimetazidine hydrochloride, nicorandil, nisoldipine, nitrendipine, nitroglycerin, nifedipine, amlodipine besylate, benidipine hydrochloride, hepronicate, verapamil hydrochloride.

Antihyperlipidemic agents include atorvastatin calcium hydrate, ezetimibe, elastase ES, clinofibrate, clofibrate, colestimide, simvastatin, soysterol, sodium dextran sulfate, nicomol, niceritrol, pitavastatin calcium, fenofibrate, pravastatin sodium, fluvastatin sodium, probucol, bezafibrate, polyenephosphatidylcholine, rosuvastatin calcium.

Other agents affecting circulatory organs include ifenprodil tartrate, indomethacin, sevelamer hydrochloride, fasudil hydrochloride hydrate, lomerizine hydrochloride, gamma-aminobutanoic acid, dihydroergotoxine mesylate, tocopheryl nicotinate, nicergoline, bosentan hydrate, meclofenoxate hydrochloride, amezinium methyl sulfate.

Antitussive agents among the agents affecting respiratory organs include ephedrine hydrochloride, clofedanol hydrochloride, cloperastine, dimemorfan phosphate, dextromethorphan hydrobromide hydrate, pentoxyverine citrate, benproperine phosphate.

Expectorant agents include L-ethylcysteine hydrochloride, L-methylcysteine hydrochloride, L-carbocysteine, ambroxol hydrochloride, fudosteine, bromhexine hydrochloride.

Antitussive expectorant agents include eprazinone hydrochloride, guaifenesin, codeine phosphate hydrate, tipepidine hibenzate.

Bronchodilator agents include aminophylline hydrate, isoproterenol hydrochloride, clenbuterol hydrochloride, mabuterol hydrochloride, methoxyphenamine hydrochloride, orciprenaline sulfate, salbutamol sulfate, fenoterol hydrobromide, tulobuterol, theophylline, terbutaline sulfate, trimetoquinol hydrochloride hydrate, procaterol hydrochloride hydrate, formoterol fumarate hydrate.

Oral rinse includes azulene sodium sulfonate.

Antidiarrheals or antiflatulents among the agents affecting digestive organs include loperamide hydrochloride, dimethicone, resistant lactobacillus preparation, bifidobacteria preparation, berberine chloride hydrate, preparation for butyric acid bacteria.

Agents for peptic ulcer include azulene sodium sulfonate, aldioxa, benexate hydrochloride betadex, omeprazole, ornoprostil, gefarnate, cimetidine, sucralfate hydrate, sulpiride, cetraxate hydrochloride, sofalcone, teprenone, troxipide, nizatidine, pirenzepine hydrochloride hydrate, famotidine, plaunotol, proglumide, polaprezinc, irsogladine maleate, misoprostol, methylmethioninesulfonium chloride, ranitidine hydrochloride, lafutidine, sodium rabeprazole, lansoprazole, clebopride malate, rebamipide, roxatidine acetate hydrochloride.

Acid suppressants include magnesium oxide, magnesium hydroxide, sodium hydrogen carbonate, precipitated calcium carbonate, magnesium aluminometasilicate.

Laxatives include senna extract, sennoside, sodium picosulfate hydrate.

Choleretic agents include anetholtrithione, ursodeoxycholic acid, trepibutone, nicotinic acid, naphthylacetic acid.

Other agents affecting digestive organs include *Mallotus japonicus* extract, azulene sodium sulfonate, cetylpyridinium chloride, dequalinium chloride, azasetron hydrochloride, itopride hydrochloride, indisetron hydrochloride, granisetron hydrochloride, cevimeline hydrochloride hydrate, tropisetron hdyrochloride, ramosetron hydrochloride, ondansetron, kitasamycin acetate, mosapride citrate, domiphen bromide, dexamethasone, trimebutine maleate, domperidone, pilocarpine hydrochloride, polycarbophil calcium, mesalazine, metoclopramide.

Salivary gland hormone preparations or thyroid or parathyroid hormonal agents include dried thyroid, thiamazole, propylthiouracil, liothyronine sodium, levothyroxine sodium hydrate.

Anabolic steroids include mestanolone, methenolone.

Adrenal hormonal agents include cortisone acetate, fludrocortisone acetate, dexamethasone, triamcinolone, hydrocortisone, prednisolone, betamesone, methylprednisolone.

Androgenic hormonal agents include methyl testosterone.

Estrogenic hormonal and progestational hormonal agents include allylestrenol, estriol, ethinyl estradiol, chlormadinone acetate, conjugated estrogen, medroxyprogesterone acetate, dydrogesterone, norethisterone, pregnanediol, fosfestrol.

Other hormonal agents include kallidinogenase, clomiphene citrate, cyclophenyl, danazol, trilostane, finasteride.

Agents affecting reproductive tract among the agents affecting genitourinary apparatus include estriol, clotrimazole, chloramphenicol, tinidazole, metronidazole.

Oxytocics include methylergometrine maleate.

Contraceptive agents include ethinyl estradiol norethisterone, ethinyl estradiol levonorgestrel, desogestrel ethinyl estradiol.

Agents for hemorrhoidal disease include venous plexus extract, tribenoside, bromelain tocopherol acetate, melilot extract.

Other agents affecting genitourinary apparatus include imidafenacin, Quercus salicina extract, oxybutynin hydrochloride, vardenafil hydrochloride hydrate, propiverine hydrochloride, sildenafil citrate, solifenacin succinate, tolterodine tartrate, silodosin, cernitin pollen extract, tamsulosin hydrochloride, naftopidil, flavoxate hydrochloride, ritodrine hydrochloride.

Other agents for each organ include gamma-oryzanol, cepharanthine.

Vitamin A and D preparations among the vitamin preparations include alfacalcidol, calcitriol, vitamin A, falecalcitriol.

Vitamin B1 preparations include dicethiamine hydrochloride, octothiamine, thiamine disulfide, bisbentiamine, fursultiamine, benfotiamine.

Vitamin B preparations include cobamamide, nicotinic acid, pantethine, hydroxocobalamin acetate, pyridoxine hydrochloride, flavin adenine dinucleotide, mecobalamin, folic acid, riboflavin butyrate, pyridoxal phosphate.

Vitamin C preparations include ascorbic acid, and vitamin E preparations include tocopherol calcium succinate, tocopherol acetate.

Vitamin K preparations include phytonadione, menatetrenone.

Other vitamin preparations include astaxanthin, fucoxanthin, lutein.

Calcium preparations among the revitalizers include calcium L-aspartate, calcium lactate hydrate.

Mineral preparations include potassium L-aspartate, potassium chloride, sodium ferrous citrate, potassium gluconate, iodine lecithin, iron sulfate hydrate.

Hemostatic agents among the agents for blood or body fluid include carbazochrome sodium sulfonate hydrate, tranexamic acid, adrenochrome monoaminoguanidine mesilate.

Agents for inhibiting blood coagulation include warfarin potassium.

Other agents for blood or body fluid include aspirin, ethyl icosapentate, sarpogrelate hydrochloride, cilostazol, ticlopidine hydrochloride, beraprost sodium, limaprost alfadex, clopidogrel sulfate.

Agents for liver disorders among the other metabolized drugs include liver hydrolysate, diisopylamine dichloroacetate, tiopronin, protoporphyrin disodium, malotilate.

Detoxifying agents include calcium disodium edetate, glutathione, sodium hydrogen carbonate, calcium folinate.

Arthrifuges include allopurinol, colchicine, probenecid, benzbromarone.

Enzyme preparations include semi-alkaline proteinase, serrapeptase, pronase, bromelain, lysozyme hydrochloride.

Diabetes drugs include acarbose, acetohexamide, pioglitazone hydrochloride, buformin hydrochloride, gliclazide, glyclopyramide, glybuzole, glibenclamide, glimepiride, chlorpropamide, tolbutamide, nateglinide, voglibose, miglitol, mitiglinide calcium hydrate, metformin hydrochloride.

Other metabolized drugs include azathioprine, adenosine triphosphate disodium salt, alendronate sodium hydrate, inosine pranobex, ipriflavone, etidronate disodium, epalrestat, everolimus, L-cysteine, levocarnitine chloride, raloxifene hydrochloride, camostat mesylate, cyclosporin, tacrolimus, mizoribine, methotrexate, sodium resedronate hydrate, leflunomide.

Cellular stimulants include adenine.

Antineoplastic agents include cyclophosphamide hydrate, melphalan, estramustine phosphate sodium, capecitabine, carmofur, tegafur, fluorouracil, methotrexate, fludarabine phosphate, etoposide, aceglatone, anastrozole, exemestane, fadrozole hydrochloride hydrate, tamoxifen citrate, toremifene citrate, tamibarotene, gefitinib, tamibarotene, bicalutamide, flutamide, procarbazine hydrochloride, imatinib mesylate, letrozole.

Anti-allergic agents include alimemazine, triprolidine hydrochloride, clemastine fumarate, chlorpheniramine maleate, diphenhydramine hydrochloride, cyproheptadine hydrochloride hydrate, promethazine hydrochloride, homochlorcyclizine hydrochloride, mequitazine, auranofin, bucillamine, amlexanox, ibudilast, ebastine, azelastine hydrochloride, epinastine hydrochloride, ozagrel hydrochloride, olopatadine hydrochloride, cetirizine hydrochloride, fexofenadine hydrochloride, oxatomide, ketotifen fumarate, zafirlukast, seratrodast, splatast tosilate, tranilast, emedastine difumarate, pranlukast hydrate, bepotastine besylate, pemirolast potassium, montelukast sodium, ramatroban, repirinast, loratadine.

Antibiotic agents include vancomycin hydrochloride, amoxicillin hydrate, cephalexin, cefaclor, cefixime, cefcapene pivoxil hydrochloride hydrate, cefdinir, cefteram pivoxil, cefpodoxime proxetil, azithromycin, enoxacin, clarithromycin, ciclacillin, josamycin, roxithromycin, levofloxacin.

Synthetic antibacterials include moxifloxacin hydrochloride, lomefloxacin hydrochloride, ofloxacin, ciprofloxacin, nalidixic acid, norfloxacin, pipemidic acid hydrate, fleroxacin.

Antivirus agents include aciclovir, adefovir pivoxil, efavirenz, emtricitabine, valaciclovir hydrochloride, entecavir hydrate, zanamivir hydrate, sanilvudin, didanosine, zidovudine, nevirapine, palivizumab, fosamprenavir calcium, saquinavir mesylate, delavirdine mesylate, lamivudine, ritonavir, ribavirin, abacavir sulfate, oseltamivir phosphate, lopinavir ritonavir.

Other chemotherapeutic agents include itraconazole, terbinafine hydrochloride, furconazole.

Other effective ingredients may be, for example, one or more agents selected from the group consisting of deoxyribonucleic acid and a salt thereof, an adenylic acid derivative including adenosine triphosphate, adenosine monophosphate and a salt thereof, ribonucleic acid and a salt thereof, a nucleic acid-related material including guanine, xanthine and a derivative thereof and a salt thereof; an animal-derived extract including deproteinized blood serum extract, splenic extract, placental extract, cock's comb extract, royal jelly; microbially-derived extract including yeast extract, lactic bacterium extract, bifidus extract, ganoderma lucidum extract; plant-derived extract including carrot extract, *Swertia japonica* extract, rosemary extract, *Phellodendoron amurense* Ruprecht extract, garlic extract, aloe extract, salvia extract, arnica extract, chamomilla recutita extract, Japanese white birch extract, *Hypericaceae* extract, eucalyptus extract, soapberry extract, *Inula britannica* extract, *Spatholobus suberectus* extract, *Cassia mimosoides* extract, *Morus alba* extract, dong quai extract, adders-wort extract, *Sophora Angustifolia* extract, *Crataegi fructus* extract, white lily extract, hop extract, polyantha extract, Coix Lachryma-Jobi extract, loofa extract, *Cnidium Officinale* extract, blueberry extract, *Haematococcus* extract, *Pfaffia* extract, ginkgo leaf extract, Asian ginseng extract, Hinokitiol, cepharanthine; α- or γ-linolenic acid, eicosapentaenoic acid, succinic acid, estradiol, glycolic acid, lactic acid, malic acid, citric acid, salicylic acid, glycyrrhizinic acid, glycyrrhetinic acid, phenylbutazone, allantoin, guaiazulene, ε-aminocaproic acid, hyaluronic acid, chondroitin, chondroitin sulfate, dermatan sulfate, heparan sulfate, heparin, keratan sulfate, cysteine and a derivative thereof and a salt thereof; collagen, elastin, keratin, deep seawater, papaya powder, zinc, DHA, glutathione, flavonoid, polyphenol, tannin, ellagic acid, nucleic acids, Chinese herbs, seaweeds, inorganic substances, and a mixture thereof.

The other ingredients to be blended without impairing disintegrating properties include agents which can be usually blended in medicine such as excipient, surfactant, lubricant, acidulant, sweetener, flavoring substance, perfume, colorant, stabilizing agent, and one or more of them can be blended. For example, surfactant (e.g., polyoxyethylene hardened castor oil, polyoxyethylene polyoxypropylene glycol, sorbitan fatty acid ester, polysorbate, glycerin fatty acid ester, sodium lauryl sulfate, etc.), blowing agent (e.g., sodium hydrogen carbonate, sodium carbonate, etc.), colorant (e.g., Food Red No. 2, Food Blue No. 2, Food Yellow No. 5, Food Lake Color, iron sesquioxide, carmine, etc.), stabilizing agent (e.g., sodium edetate, tocopherol, cyclodextrin, etc.), etc. are included. The corresponding agents described in Japanese Pharmaceutical Excipients (YAKUJI NIPPO LIMITED), Japanese Pharmacopoeia may be used as these agents.

If hard taste, acid taste or bitter taste derived from starting materials including the active ingredient may be suppressed by seasoning or flavoring, acidulant (e.g., citric acid, tartaric acid, malic acid, ascorbic acid, etc.), sweetening agent (e.g., sodium saccharin, dipotassium glycyrrhizinate, aspartame, stevia, thaumatin, etc.), flavoring substance, perfume (e.g., various fruit perfumes containing lemon oil, orange oil or strawberry, and yoghurt, mint, menthol, etc.) may be blended.

The orally rapidly disintegrating tablet of the present invention may be prepared by mixing the composition of the present invention with additives of at least one or more agents selected from lubricant, excipient, disintegrating aid or binding aid, an active ingredient, and other ingredients which can be blended in medicine, followed by compressing to mold. The compression molding is preferably carried out by a direct tableting method, in which the tableting pressure is usually 200 to 2000 kgf, preferably 250 to 1600 kgf, more preferably 250 to 1200 kgf, but varies according to the tablet sizes.

In the preparation of the orally rapidly disintegrating tablet of the present invention, lubricant may be mixed with other ingredients, followed by compressing to mold, as mentioned above, but the tablet may be also prepared by a method (i.e., external lubrication) wherein lubricant is preliminarily applied to the surface of pestle and wall surface of mortar in a compression molding machine without mixing with other ingredients and a compression molding is carried out. By this method, the orally rapidly disintegrating tablet may obtain the desired hardness and disintegrating properties. The method applying lubricant to pestle and mortar may be carried out according to the conventional known methods and by using conventional machines. The orally rapidly disintegrating tablet may also obtain the desired hardness or disintegrating properties by aging such as warming and/or humidifying according to the conventional method after compression molding.

The orally rapidly disintegrating tablet of the present invention has usually 30 to 200N, preferably 40 to 100N, of hardness. The tableting pressure varies according to the tablet sizes or forms, but for example, the tablet has 30 to 150N of hardness when the tableting pressure is 100 to 1200 kgf, and the tablet has 30 to 80N of hardness when the tableting pressure is 100 to 1000 kgf, in case that 200 mg of tablet is tableted by using pestle with 8 mm of diameter.

The orally rapidly disintegrating tablet of the present invention is mainly characterized by few loss in the tablet hardness under humid conditions. In the humid regions such as Japan, the tablet is protected by blister package to block moisture, but is taken out from the package in dosing. In patients or hospitals handling many formulations, it tends to take time from packaging to dosing due to a wide use of automatic packaging machine. In the present invention, the "few loss in the tablet hardness under humid conditions" means that in the accelerated tests under humidified conditions in the following Examples, a hardness maintenance factor is 50% or more, preferably 60% or more, most preferably 70% or more. Hardness after the accelerated test under humidified condition is 25N or more, preferably 30N or more.

The orally rapidly disintegrating tablet of the present invention may be also used as a solid preparation other than tablets intended for rapid disintegrating properties (e.g., a chewable tablet). The orally rapidly disintegrating tablet of the present invention may be also used as food such as healthy food or health-promoting food, pet food or feedstuff, agrichemical, as well as medicine, due to rapid disintegrating properties by a small amount of water.

EXAMPLES

The present invention is illustrated by Examples as follows, but the scope of the present invention is not intended to be limited thereto.

Each tablet obtained in each Example was evaluated in the following manner.
[Disintegration Time in the Oral Cavity]
The time for a tablet to completely disintegrate on the tongue in the oral cavity (n=6 per a tablet) was measured for 5 subjects, of which the average time provided the disintegration time in the oral cavity.
[Hardness of Tablet]
It was measured by using Load-cell type tablet hardness tester [PC-30, manufactured by OKADA SEIKO CO., LTD.].
[Tableting Difficulties]
The mortar and pestle of a tableting machine and a tablet after tableting were observed, and sticking and capping were analyzed.
[Accelerated Test Under Humidified Condition]
A tablet was let stand for one day at 25° C. under 75% humidity condition. A tablet hardness was measured, and hardness after accelerated test was divided by one before accelerated test to be represented on percentage and to provide a hardness maintenance factor.

Examples 1-6

Preparation of Compositions

The ingredients of the disintegrating particle compositions of Table 1 were homogeneously dispersed by water so as to be 35 parts by weight per 100 parts by weight of the entire dispersion, followed by spray-dried by using a spray drying machine (type L-8, manufactured by Ohkawara Kakohki Co., Ltd.) with 100° C. of the outlet temperature to give a fluid white spherical granulated particle.

Preparation of Disintegrating Particle Compositions

TABLE 1

| | | | | | (Unit: parts by weight) |
|---|---|---|---|---|---|
| | Mannitol | Xylitol | Magnesium aluminometasilicate | Carmellose | Disintegrant |
| Example 1 | 78 | 2 | 6 | 5 | L-HPC 9 |
| Example 2 | 75 | 2 | 6 | 15 | L-HPC 2 |
| Example 3 | 78 | 2 | 6 | 5 | Crystalline cellulose 9 |
| Example 4 | 78 | 2 | 6 | 5 | C-CMC-Na 9 |
| Example 5 | 78 | 2 | 6 | 5 | CMC-Na 9 |
| Example 6 | 78 | 2 | 6 | 5 | Crospovidone 9 |
| Comparative example 1 | 83 | 2 | 6 | 0 | Crospovidone 9 |
| Comparative example 2 | 87 | 2 | 6 | 5 | None |
| Comparative example 3 | 84 | 2 | 0 | 5 | L-HPC 9 |

L-HPC was low-substituted hydroxypropylcellulose (manufactured by Shin-Etsu Chemical Co., Ltd.), CMC-Na was carmellose sodium (manufactured by Daicel Chemical Industries, Ltd.), and C-CMC-Na was croscarmellose sodium (Ac-Di-Sol®; manufactured by Daicel Chemical Industries, Ltd.). Mannitol was manufactured by Mitsubishi Foodtech Co., Ltd., xylitol was manufactured by Mitsubishi Foodtech Co., Ltd., magnesium aluminometasilicate was manufactured by Fuji Chemical Industry Co., Ltd. (Neusilin®), and carmellose was manufactured by Nichirin Chemical Industries, Ltd. (NS-300).

Examples 7-12

Preparation 1 of Orally Rapidly Disintegrating Tablets 39.2 Parts by weight of granulated particles prepared by Examples 1-6 and Comparative examples 1-3, 40 parts by weight of aspirin, 20 parts by weight of rice starch (manufactured by Shimada Industry Co., Ltd., Micropearl), 0.2 parts by weight of menthol, 0.2 parts by weight of aspartame and 0.4 parts by weight of magnesium stearate were mixed in a vinyl bag, followed by tableting by a rotary tableting machine as 50N of setting hardness to give a tablet with 240 mg of weight, 8 mm of diameter, and 9R.

Comparative Example 7

Dry Blending

78 Parts by weight of mannitol, 2 parts by weight of xylitol, 6 parts by weight of magnesium aluminometasilicate, 9 parts by weight of low-substituted hydroxypropylcellulose, and 5 parts by weight of carmellose (manufactured by Nichirin Chemical Industries, Ltd., NS-300) were mixed in a vinyl bag. 39.2 Parts by weight of the mixture, 40 parts by weight of aspirin, 20 parts by weight of rice starch (manufactured by Shimada Industry Co., Ltd., Micropearl), 0.2 parts by weight of menthol, 0.2 parts by weight of aspartame and 0.4 parts by weight of magnesium stearate were mixed in a vinyl bag. Since the resulted powders for tableting have low density and low fluidity, any setting tablets similar to the Examples could not be obtained due to the difficulty to load into a mortar.

Tableting Test

The orally rapidly disintegrating tablets of Examples 7-12 using the granulated particles of Examples 1-6 had good molding properties for tablet, so sufficient hardness as to be 40N or more of hardness, and so sufficient disintegrating properties in the oral cavity as to be 30 seconds or below of the disintegration time in the oral cavity. In view of the moisture resistance, hardness after accelerated test were 30N or more enough for the actual use, and hardness maintenance factors were 70% or more to show enough moisture resistances. In contrast, carmellose-free Comparative example 4, disintegrant-free Comparative example 5, and inorganic excipient-free Comparative example 6 had disadvantages such as showing a lot of degradation of hardness after accelerated test, bad tableting property due to adherence, delayed disintegration time, respectively, and these were insufficient for the orally rapidly disintegrating tablet with moisture resistance.

Examples 13-15

Preparation 2 of Orally Rapidly Disintegrating Tablets

The ingredients of Table 3, 0.2 parts by weight of menthol, 0.2 parts by weight of aspartame and 0.4 parts by weight of magnesium stearate were mixed, followed by tableting by a rotary tableting machine as 50N of setting hardness to give a tablet with 240 mg of weight, 8 mm of diameter, and 9R.

Composition of Orally Rapidly Disintegrating Tablets

TABLE 3

| | | | | (Unit: parts by weight) |
| | Composition of Example 1 | Aspirin | Corn-starch | Crystalline cellulose | Hydroxypropylstarch |
|---|---|---|---|---|---|
| Example 13 | 39.2 | 40 | 20 | | |
| Example 14 | 39.2 | 40 | 10 | 10 | |
| Example 15 | 39.2 | 40 | | | 20 |

TABLE 2

| | Granulated particles | Molding pressure [kgf] | Tableting property | Disintegration time in the oral cavity [seconds] | Hardness [N] | Hardness after accelerated test [N] | Hardness maintenance factor [%] |
|---|---|---|---|---|---|---|---|
| Example 7 | Example 1 | 560-600 | good | 19.9 | 41.9 | 35.9 | 86.3 |
| Example 8 | Example 2 | 775-815 | good | 18.2 | 49.7 | 39.1 | 78.7 |
| Example 9 | Example 3 | 740-780 | good | 18.6 | 54.6 | 39.3 | 71.9 |
| Example 10 | Example 4 | 680-730 | good | 23.7 | 56.6 | 42.4 | 75.0 |
| Example 11 | Example 5 | 745-785 | good | 27.2 | 58.7 | 41.6 | 70.8 |
| Example 12 | Example 6 | 830-870 | good | 18.2 | 57.6 | 41.3 | 71.7 |
| Comparative example 4 | Comparative example 1 | 760-800 | good | 29.6 | 53.5 | 24.1 | 45.0 |
| Comparative example 5 | Comparative example 2 | 770-810 | adherent | 19.0 | 64.9 | 44.4 | 68.4 |
| Comparative example 6 | Comparative example 3 | 780-830 | good | 51.0 | 56.7 | 43.7 | 77.1 |
| Comparative example 7 | — | — | difficult for tableting | — | — | — | — |

Comparative Example 8

Dry Blending

78 Parts by weight of mannitol, 2 parts by weight of xylitol, 6 parts by weight of magnesium aluminometasilicate, 9 parts by weight of low-substituted hydroxypropylcellulose and 5 parts by weight of carmellose were mixed. 39.2 Parts by weight of the mixture, 40 parts by weight of aspirin, 20 parts by weight of cornstarch, 0.2 parts by weight of menthol, 0.2 parts by weight of aspartame and 0.4 parts by weight of magnesium stearate were mixed. Since the resulted powders for tableting have low density and low fluidity, any setting tablets similar to the Examples could not be obtained due to the difficulty to load into a mortar.

Tableting Test

TABLE 4

| | Molding pressure [kgf] | Tableting property | Disintegration time in the oral cavity [seconds] | Hardness [N] |
|---|---|---|---|---|
| Comparative example 8 | — | difficult for tableting | — | — |
| Example 13 | 820-880 | good | 26.2 | 47.1 |
| Example 14 | 480-530 | good | 23.6 | 44.4 |
| Example 15 | 770-830 | good | 26.1 | 41.9 |

The orally rapidly disintegrating tablets of Examples 13-15 using Composition of Example 1 had good molding properties for tablet, so sufficient hardness as to be 40N or more of hardness, and so sufficient disintegrating properties in the oral cavity as to be 30 seconds or below of the disintegration time in the oral cavity. In contrast, dry blended powders of Comparative example 8 could not be compressed and molded to give a tablet, and were inappropriate for preparing a tablet.

Examples 16-19

Preparation 3 of Orally Rapidly Disintegrating Tablets

The ingredients of Table 5, 0.2 parts by weight of menthol, 0.2 parts by weight of aspartame and 0.4 parts by weight of magnesium stearate were mixed, followed by tableting by a rotary tableting machine as 50N of setting hardness to give a tablet with 240 mg of weight, 8 mm of diameter, and 9R.

Composition of Orally Rapidly Disintegrating Tablets

TABLE 5

(Unit: parts by weight)

| | Composition of Example 1 | Acetaminophen | Cornstarch | Rice starch | Crystalline cellulose | CMC | Hydroxypropylstarch |
|---|---|---|---|---|---|---|---|
| Example 16 | 49.2 | 30 | | | | 20 | |
| Example 17 | 39.2 | 30 | | 20 | 10 | | |
| Example 18 | 39.2 | 30 | | | 20 | | 10 |
| Example 19 | 49.2 | 30 | 20 | | | | |

Comparative Example 9

Dry Blending

78 Parts by weight of mannitol, 2 parts by weight of xylitol, 6 parts by weight of magnesium aluminometasilicate, 9 parts by weight of low-substituted hydroxypropylcellulose and 5 parts by weight of carmellose were mixed. 49.2 Parts by weight of the mixture, 30 parts by weight of acetaminophen, 20 parts by weight of cornstarch, 0.2 parts by weight of menthol, 0.2 parts by weight of aspartame and 0.4 parts by weight of magnesium stearate were mixed. Since the resulted powders for tableting have low density and low fluidity, any setting tablets similar to the Examples could not be obtained due to the difficulty to load into a mortar.

Tableting Test

TABLE 6

| | Molding pressure [kgf] | Tableting property | Disintegration time in the oral cavity [seconds] | Hardness [N] |
|---|---|---|---|---|
| Comparative example 9 | — | difficult for tableting | — | — |
| Example 16 | 1110-1190 | good | 22.9 | 44.2 |
| Example 17 | 610-660 | good | 26.5 | 53.4 |
| Example 18 | 660-710 | good | 22.9 | 52.6 |
| Example 19 | 850-950 | good | 18.6 | 48.1 |

The orally rapidly disintegrating tablets of Examples 16-19 using Composition of Example 1 had good molding properties for tablet, so sufficient hardness as to be 40N or more of hardness, and so sufficient disintegrating properties in the oral cavity as to be 30 seconds or below of the disintegration time in the oral cavity. In contrast, dry blended powders of Comparative example 9 could not be compressed and molded to give a tablet, and were inappropriate for preparing a tablet.

Reference Example 1

Preparation of Masking Particles

Mosapride citrate was used as a bitter-tasting active ingredient to prepare masking particles according to the method of WO2005/55989. Specifically, 10 parts by weight of water was sprayed into 21 parts by weight of mosapride citrate 2 hydrate, 20 parts by weight of methylcellulose and 59 parts by weight of D-mannitol to be granulated by an agitation granulation machine, dried at 80° C. overnight, and filtered by 32 mesh sieve to prepare a masking particle.

Examples 20-21

Preparation 4 of Orally Rapidly Disintegrating Tablets

The ingredient of Table 7, 0.2 parts by weight of menthol, 0.2 parts by weight of aspartame and 0.4 parts by weight of magnesium stearate were mixed, followed by tableting by a rotary tableting machine as 50N of setting hardness to give a tablet with 240 mg of weight, 8 mm of diameter, and 9R.

Composition of Orally Rapidly Disintegrating Tablets

TABLE 7

(Unit: parts by weight)

|  | Composition of Example 1 | Particle of Reference example 1 | Corn-starch | Crystalline cellulose | Crospovidone | Hydroxy-propyl-starch |
|---|---|---|---|---|---|---|
| Example 20 | 51.2 | 25 | 10 | 10 | 3 |  |
| Example 21 | 47.2 | 25 | 10 | 10 |  | 7 |

Comparative Example 10

Dry Blending

78 Parts by weight of mannitol, 2 parts by weight of xylitol, 6 parts by weight of magnesium aluminometasilicate, 9 parts by weight of low-substituted hydroxypropylcellulose and 5 parts by weight of carmellose were mixed. 47.2 Parts by weight of the mixture, 25 parts by weight of the masking particle of Reference example 1, 10 parts by weight of cornstarch, 10 parts by weight of crystalline cellulose, 7 parts by weight of hydroxypropyl starch, 0.2 parts by weight of menthol, 0.2 parts by weight of aspartame and 0.4 parts by weight of magnesium stearate were mixed. Since the resulted powders for tableting have low density and low fluidity, any setting tablets similar to the Examples could not be obtained due to the difficulty to load into a mortar.

Tableting Test

TABLE 8

|  | Molding pressure [kgf] | Tableting property | Disintegration time in the oral cavity [seconds] | Hardness [N] | Hardness after accelerated test [N] | Hardness maintenance factor [%] |
|---|---|---|---|---|---|---|
| Comparative example 10 |  | difficult for tableting |  |  |  |  |
| Example 20 | 620-670 | good | 21.3 | 46.1 | 36.2 | 78.5 |
| Example 21 | 680-730 | good | 29.3 | 52.7 | 48.9 | 92.7 |

The orally rapidly disintegrating tablets of Examples 20 and 21 using Composition of Example 1 had good molding properties for tablet, so sufficient hardness as to be 40N or more of hardness, and so sufficient disintegrating properties in the oral cavity as to be 30 seconds or below of the disintegration time in the oral cavity. In view of the moisture resistance, hardness after accelerated test were 30N or more enough for the actual use, and hardness maintenance factors were 70% or more to show enough moisture resistances.

The invention claimed is:

1. A disintegrating particle composition, which is prepared by a process comprising dispersing in an aqueous solvent at least one inorganic excipient, at least one disintegrant, carmellose, mannitol and xylitol to obtain a dispersion, and then spray-drying the dispersion to obtain complex particles, wherein
   (a) the mannitol is in the amount of 70 to 85 parts by weight;
   (b) the xylitol is in the amount of 1 to 5 parts by weight;
   (c) the inorganic excipient(s) are in the amount of 2 to 9 parts by weight and are selected from the group consisting of magnesium aluminometasilicate, magnesium aluminosilicate, aluminum silicate, calcium silicate, magnesium silicate, anhydrous silicic acid and silicon dioxide;
   (d) the disintegrant(s) are in the amount of 2 to 9 parts by weight and are selected from the group consisting of low-substituted hydroxypropylcellulose, crystalline cellulose, croscarmellose sodium, carmellose sodium and crospovidone;
   (e) the carmellose is in the amount of 1 to 15 parts by weight, and
   the total amount of the ingredients (a) to (e) is 100 parts by weight.

2. The disintegrating particle composition of claim 1, wherein
   the carmellose is in the amount of 2 to 15 parts by weight of the total amount of ingredients.

3. The disintegrating particle composition of claim 1, wherein the inorganic excipient has an average particle size of 0.1 to 300 μm.

4. The disintegrating particle composition of claim 1, wherein the disintegrant is at least one selected from the group consisting of crospovidone, low-substituted hydroxypropylcellulose, croscarmellose sodium and crystalline cellulose.

5. An orally rapidly disintegrating tablet comprising the disintegrating particle composition of claim 1, wherein a hardness of the tablet after an accelerated test under a humidified condition is 25N or more.

6. An orally rapidly disintegrating tablet comprising the disintegrating particle composition of claim 1, 0.01 to 200 parts by weight of an active ingredient and 10 to 200 parts by weight of at least one additional additive disintegrant per 100 parts by weight of the disintegrating particle composition of claim 1.

7. The orally rapidly disintegrating tablet of claim 6, wherein the additional additive disintegrant is at least one selected from the group consisting of hydroxypropyl starch, crystalline cellulose, carmellose sodium, crospovidone, cornstarch, waxy cornstarch, rice starch, sticky rice starch, potato starch, flour starch, sweet potato starch and tapioca starch.

8. The disintegrating particle composition of claim 1, wherein the carmellose is in the amount of 1 to 5 parts by weight.

9. The disintegrating particle composition of claim 1, wherein the inorganic excipient is magnesium aluminometasilicate.

* * * * *